United States Patent [19]

Welage

[11] 4,367,745

[45] Jan. 11, 1983

[54] CONFORMABLE ELECTRICALLY CONDUCTIVE COMPOSITIONS

[75] Inventor: Norbert A. Welage, Forest Lake, Minn.

[73] Assignee: Minnesota Mining and Manufacturing Company, St. Paul, Minn.

[21] Appl. No.: 153,413

[22] Filed: May 27, 1980

[51] Int. Cl.³ ............................................. A61B 17/36
[52] U.S. Cl. ............................... 128/303.13; 128/798; 252/511; 428/327
[58] Field of Search ................................ 128/639–641, 128/644, 303.13, 798, 802; 252/511; 428/327, 344, 355

[56] References Cited

U.S. PATENT DOCUMENTS

| | | | |
|---|---|---|---|
| 3,911,906 | 10/1975 | Reinhold, Jr. | 128/641 |
| 4,066,078 | 1/1978 | Berg | 128/641 |
| 4,098,945 | 7/1978 | Oehmke | 428/327 |
| 4,237,886 | 12/1980 | Sakurada et al. | 128/303.13 |

Primary Examiner—Lee S. Cohen
Attorney, Agent, or Firm—Cruzan Alexander; Donald M. Sell; Carolyn A. Bates

[57] ABSTRACT

Improved conformable electrically-conductive compositions are disclosed comprising a soft, polar, polymeric binder; a plurality of soft, deformable, nonpolar microspheres; and an oleophilic electrically conductive filler. The compositions are particularly useful as the interface material between the skin and the electrode plate of a biomedical electrode.

12 Claims, 3 Drawing Figures

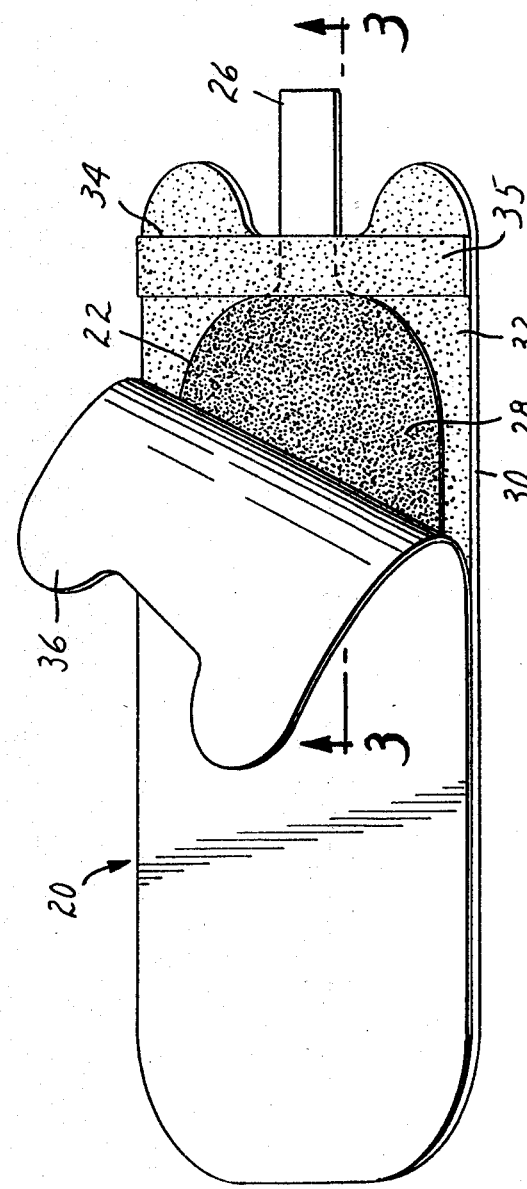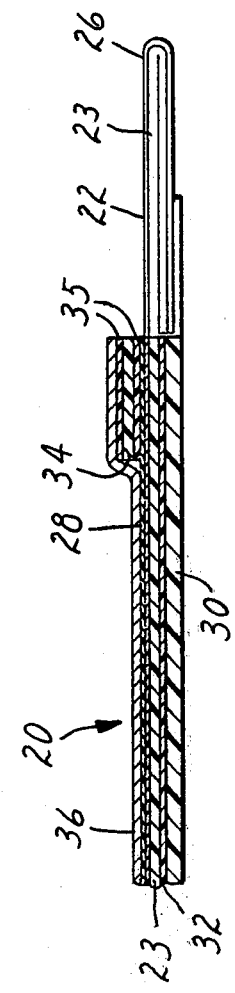

CONFORMABLE ELECTRICALLY CONDUCTIVE COMPOSITIONS

TECHNICAL FIELD

This invention relates broadly to the field of electrically conductive compositions comprising a polymeric binder and an electrically conductive filler. More particularly, it relates to conformable electrically conductive compositions comprising a polymeric binder, conductive filler and a plurality of soft, deformable microspheres. A particular embodiment of the invention relates to a biomedical electrode containing the electrically conductive composition of the invention on the skin-contacting surface thereof.

BACKGROUND ART

One particularly useful application for conformable electrically conductive compositions is as the interface material between the skin and the electrode plate of a biomedical electrode. For many years conductive materials predominately used in biomedical electrodes were messy gels containing ionizable inorganic salts and humectants to provide the requisite electrical conductivity. Such gels suffer from a number of disadvantages. Because of their high water content, they tend to dry out and lose their conductivity unless elaborately packaged. Also, when the electrode is removed from the skin, the gel leaves a messy residue on the skin requiring clean-up.

Improved alternatives to messy gels and creams have been developed in recent years and the emergence of so-called "dry" electrodes has been the result. Of these dry electrodes, at least two contain a conformable electrically conductive interface material comprising a pressure-sensitive material which has been made electrically conductive by the inclusion of a conductive filler. U.S. Pat. No. 3,911,906 describes such a biomedical electrode in which the preferred pressure-sensitive material is a synthetic acrylic copolymer and the electrically conductive filler is fine carbon powder.

German Patent Application No. DT 2814-061 describes an electrode in which the electrically conductive interface layer is a mixture of carbon fibers and an acrylate adhesive.

U.S. Pat. No. 4,098,945 describes soft conformable electrically conductive compositions comprising a soft polymeric binder such as a pressure-sensitive adhesive, an electrically conductive filler such as carbon black and a plurality of insoluble, nonconductive, deformable, normally tacky and elastomeric microspheres dispersed in the binder. The microspheres impart flexibility and conformability to the compositions while lessening the amount of conductive filler required to provide electrical conductivity. When these compositions were tested for use as the conductive interface material in a bioelectrode, particularly an electrosurgical grounding plate electrode, they were found to provide insufficient electrical conductivity. Increasing the amount of conductive particles in the composition in order to increase conductivity had an adverse effect on physical properties such as softness, conformability and tack.

It was surprisingly discovered that by using a polar polymeric binder in conjunction with non polar microspheres and oleophilic electrically conductive particles, the conductivity of the composition was greatly enhanced without increasing, and in most cases by actually decreasing, the amount of conductive particles required. Although not wishing to be bound by any specific theory, it is believed that the compositions of the present invention exhibit enhanced electrical conductivity by providing better conductive pathways through the binder. The synergistic effect of the polar binder, the nonpolar microspheres and the conductive particles results in a realignment of the conductive particles within the binder matrix. Photomicrographic analysis of the conductive compositions of the invention indicate that the conductive filler is not homogeneously dispersed throughout the binder as is the case with prior art compositions. The conductive particles concentrate around the surface of the microspheres thereby providing better electrically conductive pathways with a minimum amount of conductive filler.

DISCLOSURE OF INVENTION

According to the present invention there is provided an improved conformable conductive composition comprising: (a) a soft polymeric binder forming a coherent matrix having a Shore A hardness of less than about 40; (b) a plurality of insoluble, deformable generally non-reactive and nonconductive microspheres having Shore A harness less than about 40 dispersed in the binder in an amount from about 20 to 60 percent by weight of the composition; and (c) electrically conductive particles dispersed in the binder in an amount effective to provide at least one electrically conductive pathway through the composition. The specific improvement in the composition, which is the essence of the present invention, comprises the use of a polar polymeric binder in combination with nonpolar microspheres and oleophilic conductive particles, whereby the conductive particles have an affinity for, and concentrate at the surface of, the microspheres.

The term "polar" as used herein to describe the polymeric binder refers to polymers or copolymers wherein the electrical charges in the molecule are not symetrically distributed, i.e., the polymer or copolymer contains coordinated valence bonds between two atoms whereby one loses and the other gains a share of two electrons. Polar polymeric binders may include ionic or non-ionic materials. Generally, in the case of non-ionic polymeric binders, the requisite polarity is provided if the binder is water soluble or contains at least 15 mole percent of water soluble monomer. In the case of ionic polymeric binders, at least 10 mole percent of the monomeric units should contain ionic groups.

The term "nonpolar" as used herein to describe the microspheres refers to polymeric materials in which the electrical charges in the molecule are substantially symetrically distributed. Small amounts of polar monomer units, particularly ionic monomer units, may be present, but the overall character of the microspheres must be substantially nonpolar.

The term oleophilic as used herein to define the electrically conductive filler means that the conductive filler has an affinity for nonpolar materials.

BRIEF DESCRIPTION OF DRAWINGS

Further understanding of the invention will be facilitated by reference to the accompanying drawings wherein:

FIG. 2 is a perspective view of a surgical grounding plate electrode containing the conductive composition of the invention;

FIG. 3 is a sectional view of the grounding plate electrode of FIG. 2 through line 3—3.

Referring now to FIG. 1, the soft, conformable electrically conductive composition 10 comprises a soft polar polymeric binder 12 which serves as a matrix for a plurality (major amount) of insoluble soft nonpolar microspheres 14 and a plurality (minor amount) of oleophilic electrically conductive particles 16. The composition, as illustrated, is coated onto a metal substrate 18 such as the metal foil of a grounding plate electrode.

Figure 1:
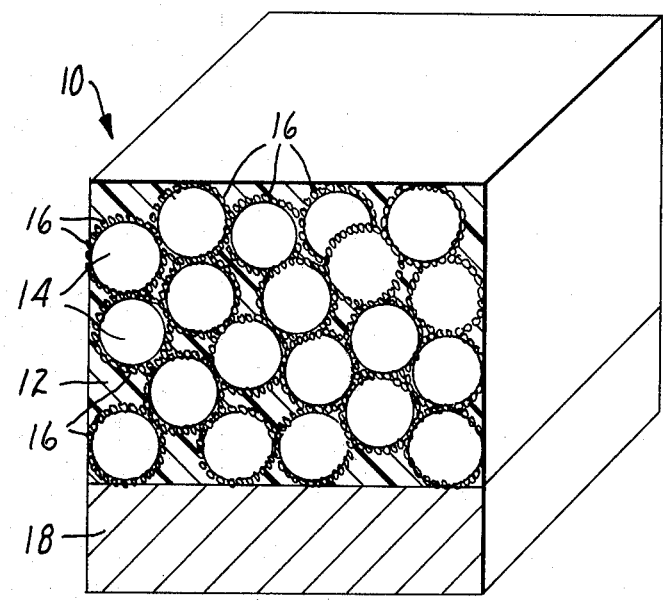
FIG. 1 is a greatly enlarged cross section of a portion of the conductive composition of the invention.

Because electrically conductive particles 16 have an affinity for the nonpolar microspheres 14, they are not homogeneously distributed throughout the binder in the spaces between the microspheres. Rather, the conductive particles are concentrated on the surface of the microspheres. It is believed that the concentration of conductive particles on the surface of the microspheres forms many highly conductive pathways and accounts for the enhanced electrical conductivity of the compositions over prior art compositions containing equivalent or greater amounts of conductive particles. By minimizing the amount of conductive particles required, the physical properties of the compositions such as conformability and tackiness are maximized.

Referring to FIGS. 2 and 3, a grounding plate electrode 20 of the type described in copending application Ser. No. 114,565, filed Jan. 23, 1980, is depicted. The electrode is comprised of an electrode plate 22 having a first surface and a second skin-contacting surface and is constructed from an electrically conductive material such as stainless steel, silver, nickel or the like, compressed carbon or graphite, or a metal coated plastic, fabric, or conductive plastic material. The preferred material for use as electrode plate 22 is aluminum. When aluminum is utilized, it is preferred that the first surface be coated with a polyester backing 23 to facilitate handling. The electrode plate has means associated therewith for electrical connecting to a lead wire which is, in turn, connected to an electromedical device. In electrode 20 the means for electrical connection to a lead wire is illustrated by connector tab 26. Connector tab 26 may be adapted to fit an electromedical connecting clip which is well known to the medical art, e.g., U.S. Pat. No. 4,061,408, or equipped with a permanent lead wire (not shown). The skin-contacting surface of the electrode plate, i.e. second surface, is coated with a layer 28 of the conductive material of the invention illustrated in FIG. 1. Overlying the polyester backing 23 and extending outward from the periphery thereof is a backing 30. Backing 30 aids in holding the electrode securely to the skin of the patient. Backing 30 is preferably made of a closed cell foam with an adhesive coating 32. The backing may be constructed from a vinyl foam tape sold as "Microfoam TM" brand surgical tape by the 3M Company, St. Paul, Minn. Another is a closed cell polyethylene foam, sold as "Volara TM" brand foam by the Voltex Corporation of Lawrence, Mass. The adhesive 32 may be of the type disclosed in U.S. Pat. No. 2,973,286. An insulating strip 34 of polyethylene may be added if it is believed that the connector tab 26 is in need of additional insulation at the portion nearest the means for external electrical connection. Optionally, insulating strip 34 may have a double-sided adhesive coating 35 of material similar to that of adhesive layer 32 which would allow strip 34 to aid in the securing of the electrode to the patient. An optional release liner 36 may be attached to the adhesive-coated surfaces of the electrode 20 in order to preserve the adhesive character until ready to use. Such release liners are well known in the art.

DETAILED DESCRIPTION

The binder systems useful in the present invention can be any soft or rubbery polar material or any material capable of being cured to a soft rubbery state, which will form a coherent matrix for the microspheres and conductive filler. As noted previously, the binder should be capable of providing a composition having a Shore A hardness of less than about 40. Plasticizers, preferably glycerol or other polyhydric alcohols, may be added to achieve the requisite conformability.

In the preferred embodiment of the invention, the polar binder system is a pressure-sensitive adhesive so that the entire conductive composition will immediately adhere to conductive surfaces upon contact. When the compositions of the invention are used as the conductive interface between the skin and an electrode plate, it is obviously important that the binder system be dermally-nonirritating.

Examples of suitable non-ionic polar binder systems useful according to the invention are disclosed in U.S. Pat. No. 4,273,135, the disclosure of which is incorporated herein by reference. Briefly, the non-ionic polar polymeric materials disclosed therein which are useful in the compositions of the present invention are classified as follows:

A. non-ionic water-soluble polymers;
B. non-ionic water-soluble interpolymers of water-soluble monomers and water-insoluble monomers;
C. non-ionic polar water-insoluble interpolymers of water-soluble monomers and water-insoluble monomers that contain at least 15 mole percent of interpolymerizable water-soluble monomer.

The polymers of Class A, non-ionic water-soluble synthetic polymers, are well known and a great many have been prepared. All are suitable for use in the invention if they are film-forming; generally, a weight-average molecular weight of about 10,000 will make them film-forming. Examples of Class A polymers are: hydroxyalkylcelluloses such as 2-hydroxyethylcellulose; and synthetic polymers of water-soluble monomers.

Water-soluble monomers which can be homopolymerized or interpolymerized with other members of the series to give Class A water-soluble non-ionic polymers in accordance with well known methods include the following vinyl monomers:

acrylic acids such as acrylic and methacrylic acids;
olefinic polycarboxylic acids such as maleic acid, fumaric acid, itaconic acid, aconitic acid, and citraconic acid;
acrylamides such as acrylamide, methacrylamide, N-alkylacrylamides such as N-methylacrylamide, N-butylacrylamide, and N-methylmethacrylamide;
vinyl alcohol, obtained by polymerization of vinyl acrylates, such as vinyl acetate and hydrolysis of the resulting polymer;
N-vinyl lactams such as N-vinyl pyrrolidone;
2-vinyl imidazoline as disclosed in U.S. Pat. No. 3,557,061;
2-vinyl tetrahydropyrimidine as disclosed in U.S. Pat. No. 3,557,061;
vinyl pyridines such as 2-, 3- and 4-vinyl pyridine;

aminoalkylacryl compounds, e.g., N-(2-dimethylaminoethyl)acrylamide, N-(2-dimethylaminopropyl)acrylamide, N,N-bis(2-dimethylaminoethyl)acrylamide and N-(4-dimethylamino cyclohexyl)acrylamide and aminoalkylacrylates such as 2-dimethylaminoethyl acrylate, 2-dimethylaminopropyl acrylate and 3-diethyl-aminopropyl methacrylate;

vinyl ethers such as vinyl methyl ether;

Still other monomers that may be polymerized to Class A water-soluble polymers are ethylene oxide and ethyleneimine.

The non-ionic hydrophilic interpolymers of Class B result from interpolymerization of major amounts of the addition-polymerizable, water-soluble monomers listed above with minor amounts of non-ionic addition-polymerizable, water-insoluble monomers such as:

acrylate esters such as methyl acrylate, methyl methacrylate, butyl acrylate, iso-octyl acrylate, 2-ethylhexyl acrylate, dodecyl methacrylate, octadecyl methacrylate, and cyclohexyl acrylate;

vinyl ethers such as 2-ethylhexyl vinyl ether, decyl vinyl ether, and octadecylvinyl ether;

vinyl acrylates such as vinyl acetate, vinyl butyrate, and vinyl dodecanoate;

olefins such as ethylene, propylene, styrene, α-methylstyrene, 4-chlorostyrene, iso-butylene, and vinylcyclohexane;

olefinic polycarboxylic acid esters such as dimethyl maleate, dimethyl fumarate, and diethyl itaconate; and vinyl halides such as vinyl chloride and vinylidene dichloride.

As is apparent to one skilled in the art, the minimum concentration of the water-soluble monomers necessary to confer water-solubility on the interpolymer will vary considerably depending on the nature of both the water-soluble and the water-insoluble monomers.

The preferred non-ionic polar polymers of the invention are those of Class C. The Class B interpolymers discussed above represent a special kind of Class C interpolymers with the former being differentiated by their solubility in water. The Class C interpolymers, though not water-soluble, are polar and are prepared using the same addition-polymerizable non-ionic water-soluble and water-insoluble monomers discussed above. The advantage attributable to the Class C materials is that they generally provide better pressure sensitive adhesive materials.

Examples of non-ionic polar binder systems for use in the invention are listed in the following Table I. All ratios are molar ratios.

TABLE I

| Class A Polymers |
| --- |
| Poly(acrylic acid) |
| Poly(methyacrylic acid) |
| Poly(vinyl alcohol) |
| Poly(vinylpyrrolidone) |
| Poly(vinyl methyl ether) |
| Copoly(methyl vinyl ether:maleic acid) (50:50) |
| Poly(acrylamide) |
| Poly(oxyethylene) |
| Poly(ethyleneimine) |
| Class B Interpolymers |
| Copoly(vinyl acetate:vinyl alcohol) (30:70) |
| Copoly(n-butyl acrylate:acrylic acid) (5:95) |
| Copoly(2-ethylhexyl |

TABLE I-continued

| methacrylate:methacrylic acid) (2:98) |
| --- |
| Class C Interpolymers |
| Copoly (iso-octyl acrylate:acrylic acid) (61:39) |
| Copoly (iso-octyl acrylate:acrylic acid) (48:52) |
| Copoly (butyl acrylate:itaconic acid) (67:33) |
| Copoly (lauryl methacrylate:methacrylic acid) (34:66) |
| Copoly (vinyl acetate:vinyl alcohol) (70:30) |
| Copoly (vinyl chloride:vinyl alcohol) (60:40) |
| Copoly (ethylene:vinyl alcohol) (60:40) |
| Copoly (butyl acrylate:3-dimethylaminopropylacrylamide) (60:40) |

The presently preferred polymeric binders for use in the conductive compositions of the invention are ionic polymers containing at least ten mole percent of monomer units containing a cation or an anion.

Examples of useful anionic polymer binders are carboxylate-containing polymers such as those disclosed in copending application Ser. No. 155,191 filed June 2, 1980, the disclosure of which is incorporated herein by reference. Briefly, the carboxylate-containing polymers disclosed in the aforementioned application which are useful in the compositions of the present invention are classified as follows:

A. water-soluble carboxylate-containing polymers;

B. water-soluble carboxylate-containing interpolymers; and

C. polar water-insoluble interpolymers of water-insoluble monomers and at least 10 mole percent of water-soluble monomers containing carboxylate functionality.

The water-soluble carboxylate-containing polymers of Class A are prepared in accordance with well known methods by homopolymerization of a carboxylate salt or interpolymerization of two or more carboxylate salts. Suitable carboxylate salts are derived from the acid-base reaction of a base such as: (1) a Group I (Periodic Table) metal hydroxide, carbonate or bicarbonate; (2) an amine; or (3) a quaternary ammonium hydroxide, carbonate or bicarbonate; with an olefinic, addition-polymerizable carboxylic acid such as acrylic acid, methacrylic acid, maleic acid, fumaric acid, itaconic acid, aconitic acid, and citraconic acid. Alternatively, the olefinic, addition-polymerizable carboxylic acid or acids can be homo- or interpolymerized and subsequently reacted with the above-described bases to form the water-soluble carboxylated polymers. The latter method of preparation is generally preferred because higher molecular weight polymers are obtained.

The water-soluble carboxylated interpolymers of Class B are prepared by interpolymerization of the olefinic, addition-polymerizable carboxylic acids described above and olefinic, addition-polymerizable monomers free of carboxylic acid functionality which include, but are not limited to:

acrylate esters such as methyl acrylate, methyl methacrylate, butyl acrylate, iso-octyl acrylate, dodecyl methacrylate, octadecyl methacrylate, and cyclohexyl acrylate;

vinyl ethers such as methyl vinyl ether, 2-ethyl-hexyl vinyl ether, decyl vinyl ether, and octadecyl vinyl ether;

vinyl acrylates such as vinyl acetate, vinyl butyrate, and vinyl dodecanoate;

olefins such as ethylene, propylene, styrene, α-methylstyrene, 4-chlorostyrene, iso-butylene, and vinylcyclohexane;

olefinic multi-functional carboxylic acid esters such as dimethyl maleate, dimethyl fumarate, and diethyl itaconate; and vinyl halides such as vinyl chloride and vinylidene dichloride.

Class B interpolymers are prepared by well known polymerization techniques and are transformed into water-soluble carboxylate-containing interpolymers in a similar fashion as described above with the Class A polymers by a neutralization reaction with a base such as: (1) a Group I metal hydroxide, carbonate or bicarbonate; (2) an amine; or (3) a quaternary ammonium hydroxide, carbonate or bicarbonate.

The polar, water-insoluble carboxylate-containing interpolymers of Class C represent a special class of Class B interpolymers differentiated by their solubility in water. They are prepared using the same monomers and procedures as in Class B, except the carboxylate-containing monomer is present at a level below that which would yield a water-soluble interpolymer, e.g., below about 25 mole percent depending on the non-carboxylate-containing, olefinic, addition-polymerizable comonomers employed. Class C materials are generally better pressure sensitive adhesives.

Examples of carboxylate-containing polymeric binders for use in the compositions of the invention are listed in the following Table II:

TABLE II

Class A Polymers
Poly(acrylic acid)neutralized with sodium hydroxide.
Poly(acrylic acid)neutralized with triethanolamine.
Poly(acrylic acid)neutralized with ammonia.
Poly(methacrylic acid)neutralized with triethylamine.

Class B Interpolymers*
Copoly(butylacrylate:acrylic acid) (63:37) neutralized with methyldiethanolamine
Copoly(iso-octyl acrylate:acrylic acid) (60:40) neutralized with methyldiethanolamine.
Copoly(butyl acrylate:methacrylic acid) (50:50) neutralized with tetramethylammonium hydroxide.
Copoly(2-ethylhexyl methacrylate:acrylic acid) (60:40) neutralized with triethylamine.
Copoly(methyl vinyl ether:maleic acid) (50:50) neutralized with sodium carbonate.
Copoly(2-ethylhexyl vinyl ether:maleic acid) (50:50) neutralized with methyldiethanolamine.

Class C Interpolymers
Copoly(iso-octyl acrylate:acrylic acid) (90:10) neutralized with triethylamine.
Copoly(butyl acrylate:methacrylic acid) (85:15) neutralized with methyldiethanolamine.
Copoly(butyl acrylate:acrylic acid) (85:15) neutralized with tetramethylammonium hydroxide.

*All ratios are given as molar ratios.

It is obvious that one skilled in the art could vary the extent of neutralization of the carboxyl groups so as to maximize the adhesive properties of the polymer.

Other examples of ionic polymeric binders suitable for use in composition of the invention are disclosed in U.S. Pat. No. 4,066,078 and include: (1) polymers or copolymers derived from the polymerization of an ester of an α-, β-olefinically unsaturated carboxylic ester and an alcohol having a quaternary ammonium group; and (2) sulfated cellulose esters.

When any of the previously described nonionic or ionic polymers alone are not sufficiently conformable under use conditions, they can generally be brought within the prescribed limits by plasticization. Plasticization of the polymer or interpolymer can be generally accomplished by adding a more "fluid" ingredient to the polymer. Generally, it is desirable that this external plasticizing agent be compatible with the polymer. Suitable plastizers include poly(hydric alcohols) such as glycerol, poly(oxyalkylene) alcohols such as poly(oxypropylene) glycol, and the like.

It is also contemplated within the scope of the invention to tackify the formulations herein described, where necessary, especially to prepare a pressure sensitive adhesive formulation which is a preferred embodiment of the invention. Preferred tackifiers are the water-soluble neutralization products of naturally occurring, normally water-insoluble acid rosins (typically having an acid number in the range of 135-170, although rosins having acid numbers outside this range may also be used) and secondary or tertiary alkanolamines. Especially preferred tackifiers are the water-soluble neutralization products of hydrogenated abietic acid.

Microspheres useful in the electrically conductive compositions of the invention are those described in U.S. Pat. No. 4,098,945. The microspheres must be soft, conformable, generally nonreactive and essentially nonpolar. The size of the microspheres will generally range from about 5 to 250 microns in diameter, and preferably about 6 to 80 microns. The preferred average size of the microspheres is about 50 microns. Generally the composition contains about 20 to 60 percent microspheres by weight of the total composition. About 45 to 55 percent by weight of microspheres is preferred.

As disclosed in U.S. Pat. No. 4,098,945, the preferred soft deformable microspheres are acrylic microspheres prepared as described in the aforementioned patent. These microspheres are elastomeric polymers which are uniformly spherical, solvent insoluble and of small size. The acrylate microspheres consist essentially of about 90 to about 99.5% by weight of at least one alkyl acrylate ester and about 10 to about 0.5% by weight of at least one monomer selected from the group consisting of substantially oil-insoluble, water-soluble ionic monomers and maleic anhydride. Preferably, the microspheres comprise about 95 to about 99% by weight acrylate monomer and about 5 to 1% by weight ionic monomer, maleic anhydride, or a mixture thereof. Because the level of ionic monomer is very low, the resulting microspheres are essentially nonpolar as required for the present invention.

The alkyl acrylate ester portion of these microspheres consists of those alkyl acrylate monomers which are oleophilic, water-emulsifiable, of restricted water-insolubility and which, as homopolymers, generally have glass transition temperatures below about −20° C. Alkyl acrylate ester monomers which are suitable for use in preparing these microspheres include iso-octyl acrylate, 4-methyl-2-pentyl acrylate, 2-methyl-butyl acrylate, sec-butyl acrylate, and the like. Acrylate monomers with glass transition temperatures higher than −20° C. (i.e., tert-butyl acrylate, iso-bornyl acrylate or the like) may be used in conjunction with one of the above-described acrylate ester monomers.

The water-soluble ionic monomer portion of these microspheres is comprised of those monomers which are substantially insoluble in oil. By substantially oil-insoluble and water-soluble it is meant that the monomer has a solubility of less than 0.5% by weight and, a distribution ratio at a given temperature (preferably 50°–65° C.), of solubility in the oil phase monomer to solubility in the aqueous phase of less than about 0.005.

Examples of ionic monomers conforming to the preceding criteria include sodium methacrylate, ammonium acrylate, sodium acrylate, acrylamide and trimethylamine methacrylimide.

The copolymer microspheres are small in size, having diameters in the range of about 1 to about 250 microns, the diameter of the majority of the spheres falling in the range of about 5 to about 150 microns. The spheres are normally tacky and elastomeric, are insoluble in organic solvents, and form suspensions in all common solvents except highly polar solvents such as water, methanol, and ethanol. Typical useful solvents are ethyl acetate, tetrahydrofuran, heptane, 2-butanone and other ketones, benzene, cyclohexane, esters, iso-propanol, and higher alcohols. When dispersed, the microspheres absorb the solvent and swell to about twice their original diameter, or about eight times their original volume. After dispersion, the microspheres, which contain about 80% solvent, remain homogeneously dispersed for extended periods of time. When the dispersed microspheres are sprayed or coated on a surface, the solvent quickly evaporates, the microspheres shrinking to approximately their original size. A force applied directly to one of the polymer spheres will deform it; however, the spherical shape is reassumed upon release of the stress. Upon being heated, the spheres do not melt or flow, but retain their integrity until carbonization temperature is reached. Tack properties of the microspheres may be altered by inclusion of various resins in the solvent or aqueous suspensions of microspheres.

The electrically conductive filler used in the compositions of the invention should be of a particulate configuration and oleophilic, i.e., have an affinity for nonpolar materials. Carbon black and graphite are preferred because they are conductive and naturally oleophilic. Metallic particles will work if their surface is naturally oleophilic or if modified with a keying agent to make them more oleophilic. An example of such metallic particles is powdered aluminum treated with decyl phosphonate.

The average size of the particulate material and the amount present in the composition will vary with the type of conductive material used. A surprisingly low amount of conductive filler is necessary. For example, with the preferred conductive filler, carbon black, it is preferred that the particles have an average size of from about 1 to 15 microns and are present in the composition at from about 3 to 5 percent by weight.

The compositions are preferably made by adding a plasticizer such as glycerol or other polyhydric alcohol to an aqueous suspension of microspheres (e.g. 67% solids). To this emulsion is then added the polymer solution (e.g., ethyl acetate solvent). The resulting mixture is quite thick and is allowed to stand in order to permit the microspheres to swell. The electrically conductive filler is then added along with a solvent such as ethanol which shrinks the microspheres.

It is contemplated within the scope of the invention that the polymeric binder system may be crosslinked, if necessary, to achieve the desired physical properties. In the preferred compositions, which are opaque due to the presence of carbon black, electron beam crosslinking is preferred. A small amount of a multifunctional monomer may be included in the polymeric binder in order to increase the efficiency of the E-beaming.

The compositions may be used in any application where a conformable conductive composition is desired to provide electrical conductivity between two conductive surfaces. A preferred application is as a coating on the skin-contacting surface of an electrosurgical grounding plate electrode of the type described in co-pending application Ser. No. 114,565, filed Jan. 23, 1980. Such a grounding plate electrode comprises: (1) an electrically conductive metal film, e.g., aluminum, having an upper surface and a lower, skin-contacting surface and means for attachment of a lead wire; (2) a non-conductive backing laminated to the top surface of the metal film to facilitate handling; and (3) the electrically-conductive composition of the present invention coated on the skin-contacting surface of the metal film.

The compositions of the invention provided a high degree of electrical conductivity using a low level of conductive filler due to the novel orientation of the conductive filler on the surfaces of the microspheres.

The invention is further illustrated by way of the following non-limiting examples.

EXAMPLE 1

Glycerol (33.5 g) was mixed with an aqueous suspension of adhesive microspheres (iso-octylacrylate:acrylamide, 96:4) (50 g, 67% solids). To this mixture was added a solution of a copolymer of iso-octylacrylate:acrylic acid (50:50 by weight), neutralized with methyl diethanolamine in acetone/ethanol/water; (162 g, 20.6% solids). The mixture was allowed to stand for 18 hours and carbon black (2.7 g) ("Ketjenblack" EC, Armak Co., Chicago, Ill.) ground in an industrial blender to an average particle size of about 1 to 15 microns, was added and mixed well. Ethanol (20 g) was then added. The resulting slurry could be coated and dried to produce an electrically conductive, pressure sensitive adhesive. The impedance of a two square inch area of the material (5.1 mil thick) at 500 KHz was 6 ohms.

EXAMPLE 2

An ethylacetate solution (15 g, 26% solids) of a copolymer of butyacrylate (75 parts) and acrylic acid (25 parts), 95 mole percent neutralized with methyl diethanolamine, plus a phenyl-terminated polyethylene oxide plasticizer ("Pycal" 94, ICI) (20 parts) and a hydrogenated abietic acid tackifier ("Foral" AX, Hercules) (30 parts) was added to a suspension of adhesive microspheres (iso-octylacrylate:acrylamide, 96:4) in ethylacetate (35.5 g, 11% solids) followed by glycerol (0.78 g) and carbon black (described in Example 1), in ethylacetate (4.4 g, 7% solids). This was mixed well and ethanol (30 g) was added. The resulting slurry could be coated and dried to form a pressure sensitive adhesive with good electrical conductivity. The impedance of a two square inch area of the material (5.1 mil thick) at 500 KHz was 1.8 ohms.

EXAMPLE 3

Glycerol (33.5 g) was mixed with an aqueous suspension of adhesive microspheres (iso-octylacrylate:acrylamide, 96:4) (50 g, 67% solids). To this was added a solution of a copolymer of isooctylacrylate:acrylic acid (50:50 by weight), neutralized with methyldiethanolamine; in acetone/ethanol/water; (162 g, 20.6% solids). The mixture was allowed to stand for 18 hours. Powdered aluminum (#400 atomized powder, Reynolds Metals Co., Louisville, Ky.) (8.2 g) was suspended in ethanol (5 g) and decylphosphonate (1.5 g) was added. The mixture was stirred for three hours and then added to the first mixture. Ethanol (15 g) was added and thoroughly mixed. The resulting material could be coated and dried to yield an electrically conducting pressure sensitive adhesive. The impedence of a two square inch area of the material (8 mil thick) at 500 KHz was 24 ohms. A similar sample prepared identically without the decylphosphonate had an impedence of 38 ohms.

What is claimed is:

1. In a comformable conductive composition comprising: (a) a soft polymeric binder forming a cohesive matrix having a Shore A hardness of less than about 40; (b) a plurality of insoluble, deformable, generally nonreactive microspheres having Shore A hardness less than about 40 dispersed in said binder in an amount from about 20 to 60 percent by weight of said composition; and (c) electrically conductive particles dispersed in said binder in an amount effective to provide at least one electrically conductive pathway through said composition; the improvement wherein said polymeric binder is polar, said microspheres are nonpolar, said conductive particles are oleophilic, and said conductive particles have an affinity for said microspheres and concentrate at the surface of said microspheres.

2. The composition according to claim 1 wherein said polymeric binder is a pressure sensitive adhesive.

3. The composition according to claim 2 wherein said polymeric binder is comprised of monomer units at least 10 percent of which contain an ionic group.

4. The composition according to claim 3 wherein said binder is poly(butylacrylate:acrylic acid) neutralized with methyldiethanolamine.

5. The composition according to claim 1 wherein said polymeric binder contains a plasticizer.

6. The composition according to claim 5 wherein said plasticizer is a polyhydric alcohol.

7. The composition according to claim 6 wherein said polyhydric alcohol is glycerol.

8. The composition according to claim 1 wherein said microspheres consist essentially of about 90 to about 99.5 percent by weight of at least one alkyl acrylate ester and about 10 to about 0.5 percent by weight of at least one monomer selected from the group consisting of substantially oil-insoluble, water soluble ionic monomers and maleic anhydride.

9. The composition according to claim 8 wherein said microspheres consist essentially of about 96 percent by weight iso-octylacrylate and about 4 percent by weight acrylamide.

10. The composition according to claim 1 wherein said conductive particles are carbon black.

11. The composition according to claim 1 wherein said conductive particles are aluminum powder treated with a keying agent to render it oleophilic.

12. In a grounding plate electrode comprising an electrically-conductive metal film having an upper surface and a lower, skin-contacting surface; means for attaching a lead wire to said metal film; a backing laminated to said upper surface; and a layer of a conformable, electrically-conductive composition on said skin-contacting surface; the improvement wherein said electrically conductive composition comprises: (a) a soft polar polymeric binder forming a cohesive matrix having a Shore A hardness of less than about 40; (b) a plurality of insoluble, deformable, generally non-reactive, non-polar microspheres having a Shore A hardness less than about 40 dispersed in said binder in an amount from about 20 to 60 percent by weight of said composition; and (3) oleophilic electrically conductive particles dispersed in said binder in an amount effective to provide at least one electrically conductive pathway through said composition, said conductive particles having an affinity for said microspheres and being concentrated at the surface of said microspheres.

* * * * *